United States Patent [19]
Genna

[11] Patent Number: 6,015,974
[45] Date of Patent: *Jan. 18, 2000

[54] SCINTILLATION CAMERA WITH IMPROVED SCINTILLATION MATERIAL SEGMENT INTERFACES

[75] Inventor: Sebastian Genna, Belmont, Mass.

[73] Assignee: Digital Scintigraphics, Inc., Waltham, Mass.

[*] Notice: This patent is subject to a terminal disclaimer.

[21] Appl. No.: 08/897,714

[22] Filed: Jul. 21, 1997

Related U.S. Application Data

[63] Continuation-in-part of application No. 08/543,870, Oct. 19, 1995, Pat. No. 5,652,429.

[51] Int. Cl.[7] .................................................. G01T 1/202
[52] U.S. Cl. ........................ 250/368; 250/367; 250/366
[58] Field of Search ................................... 250/366, 367, 250/368

[56] References Cited

U.S. PATENT DOCUMENTS

| | | | |
|---|---|---|---|
| 4,532,425 | 7/1985 | Abileah et al. | 250/363.02 |
| 4,700,074 | 10/1987 | Bosnjakovic | 250/363.02 |
| 4,778,995 | 10/1988 | Kulpinski et al. | 250/586 |
| 4,831,263 | 5/1989 | Yamashita | 250/368 |

*Primary Examiner*—Constantine Hannaher
*Assistant Examiner*—Darren M. Jiron
*Attorney, Agent, or Firm*—Iandiorio & Teska

[57] ABSTRACT

A scintillation camera including photosensors for producing an output in response to emitted light; a scintillation material for emitting light directed to the photosensors in response to radiation absorbed by a source, the scintillation material formed in two or more segments defining an optical interface between adjacent segments; and an increased surface area at the interface for improving the transmissivity of the interface and efficiently optically coupling the adjacent sensors.

16 Claims, 11 Drawing Sheets

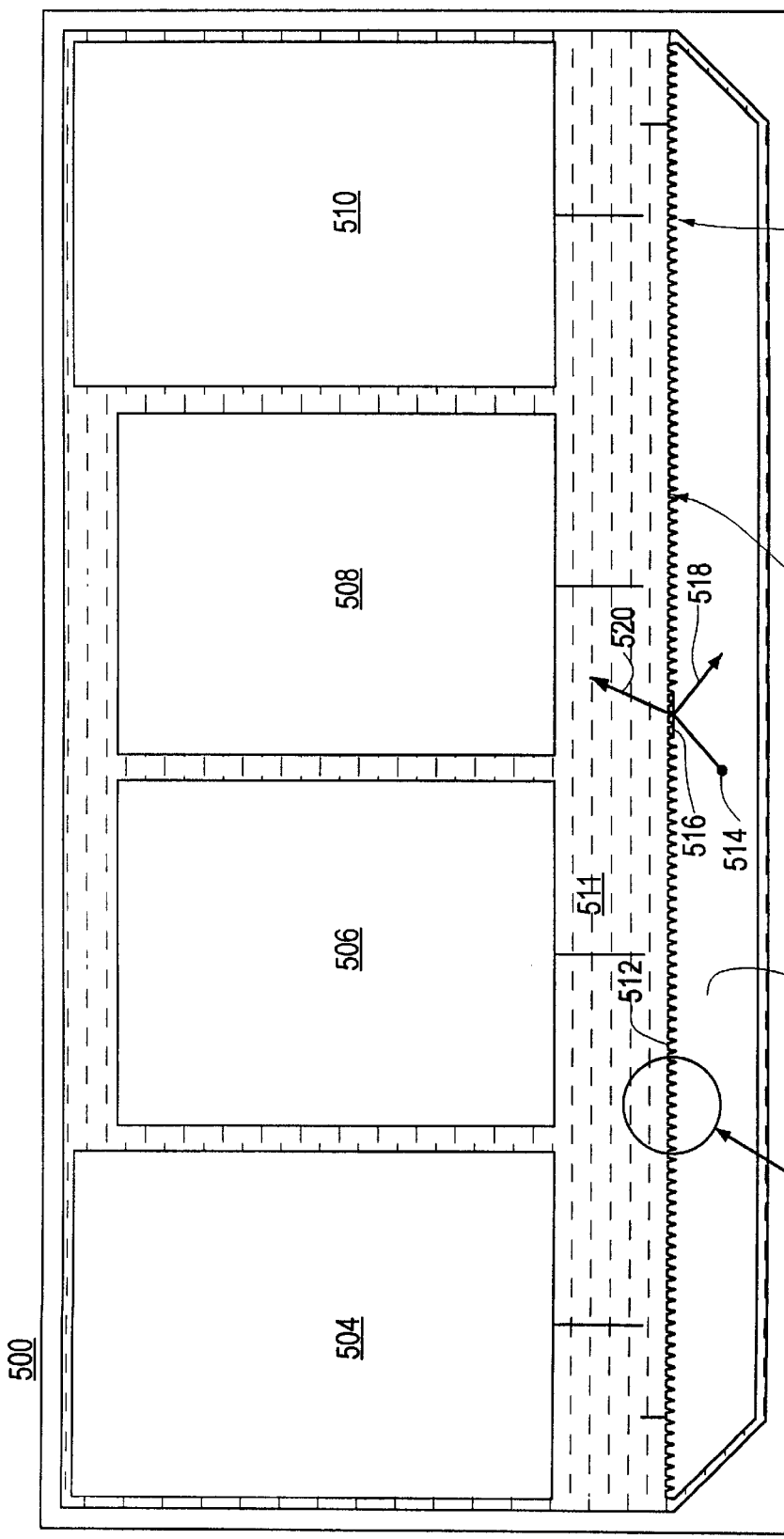
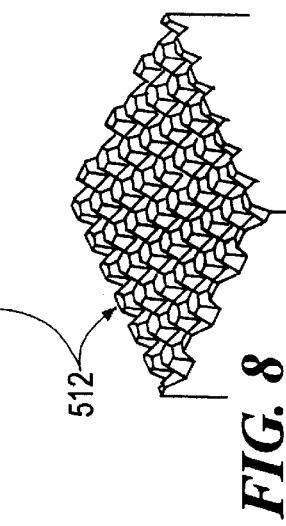
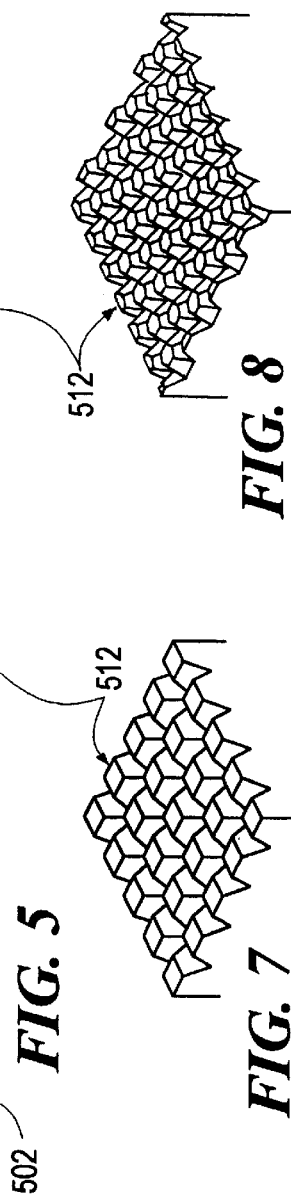
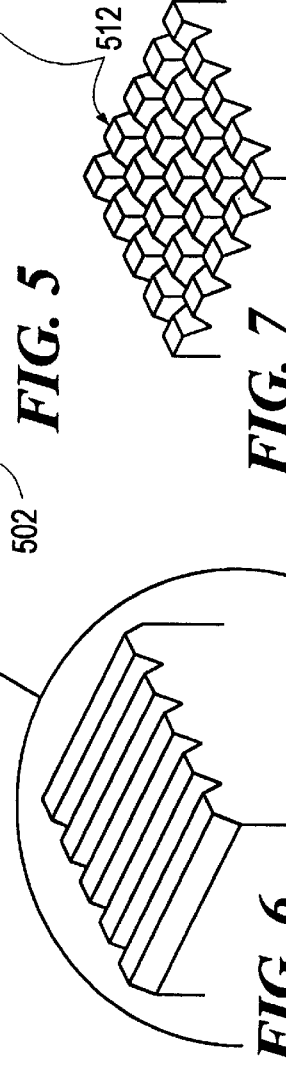

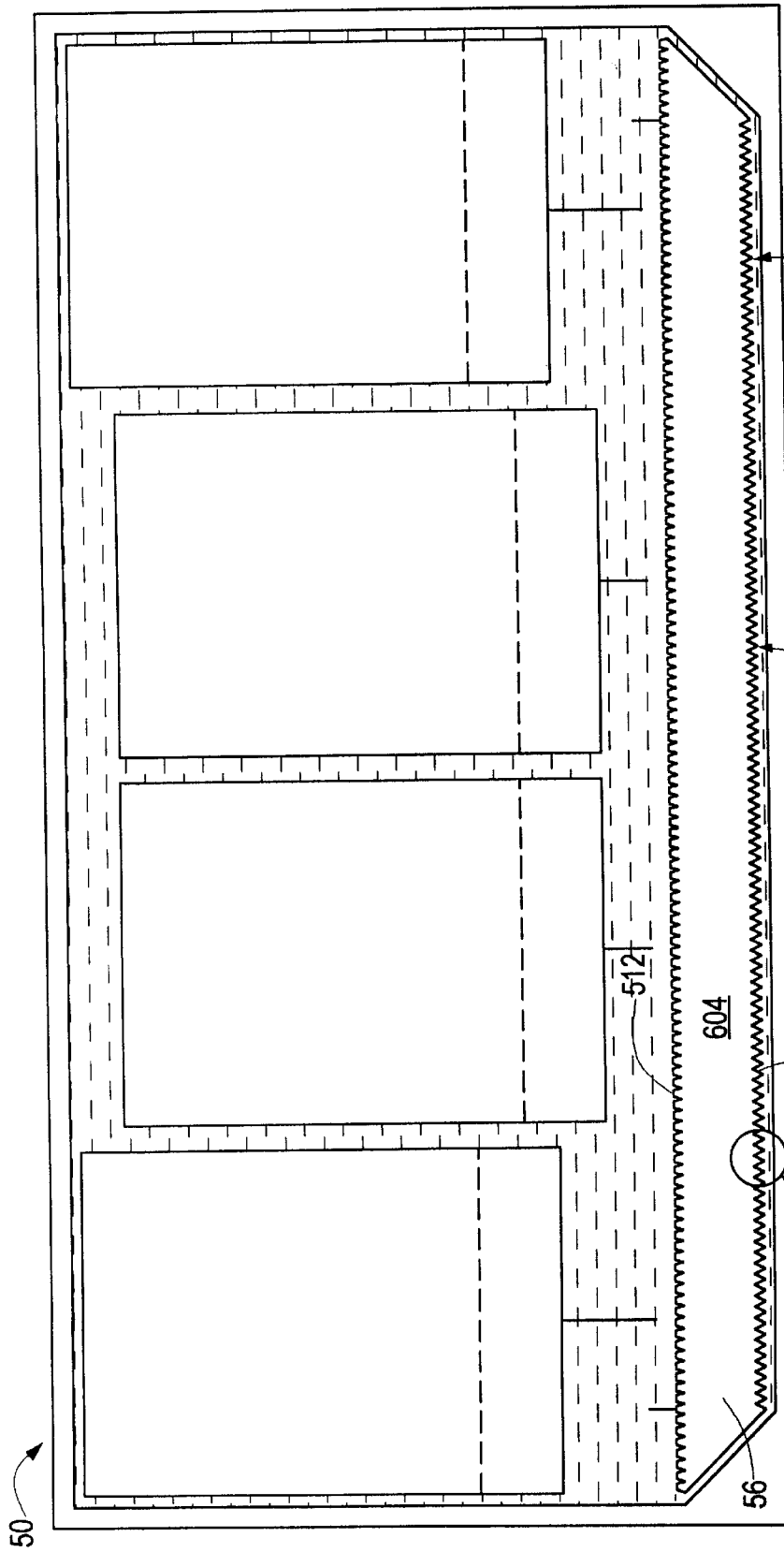
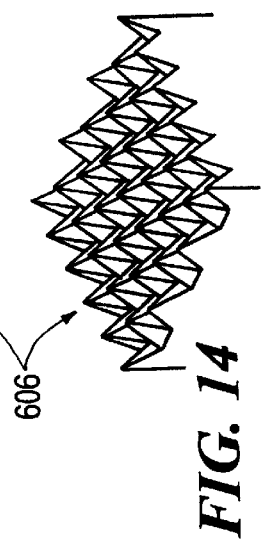
FIG. 14
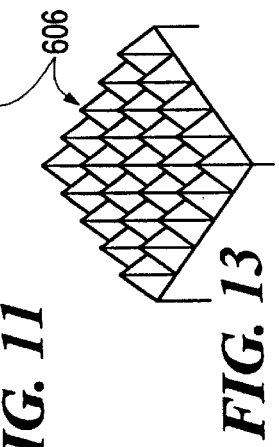
FIG. 13
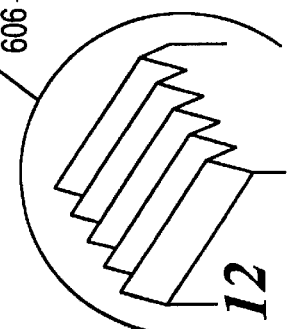
FIG. 11
FIG. 12

SCINTILLATION CAMERA WITH IMPROVED SCINTILLATION MATERIAL SEGMENT INTERFACES

RELATED CASES

This application is a Continuation-In-Part application of U.S. application Ser. No. 08/543,870 filed Oct. 19, 1995 now U.S. Pat. No. 5,652,429 issued Jul. 29, 1997 entitled "Liquid Interface Scintillation Camera".

FIELD OF INVENTION

This invention features a scintillation camera with improved scintillation material segment interfaces for improving the transmissivity at the interfaces and efficiently optically coupling adjacent scintillation material segments.

BACKGROUND OF INVENTION

Radionuclide emission scintillation cameras, also called Anger cameras, are used to image the distribution of gamma-ray radioactive material within a body part or organ, such as the brain or the breast, for example, for diagnostic purposes. A source of penetrating radiation is administered to the patient, which typically consists of a pharmaceutical tagged with a gamma-ray emitting radionuclide (radiopharmaceutical) designed to go to and deposit in the organ or elements of the body under diagnostic examination, such as, for example, in the detection of a tumor. Gamma-rays emitted by the radiopharmaceutical are received and detected by the camera, the position of each detected ray event is determined, and the image of the radioactivity distribution in the organ or other body part is constructed by known techniques from an accumulation of events.

Scintillation cameras generally employ an optically continuous crystal of thallium activated sodium iodide, NaI(Tl), as a gamma-ray energy transducer. The energy of the gamma-rays are absorbed in the crystal and are converted to light emissions called scintillation events, each event having an energy proportional to the energy of the absorbed gamma-rays. In conventional cameras, light is transmitted from the crystal to an optically clear glass window through a silicone gel interface that fills a thin separation between the glass window and the crystal. The optical window is part of a container which seals the crystal from air and humidity which would otherwise oxidize the crystal and degrade its optical clarity. An array of photomultiplier (PM) tubes is optically coupled to the glass window, typically by means of optically coupling grease, in order to transmit light to photocathodes located on the inner surface of the glass entrance face of each photomultiplier tube. Thus, the scintillation light events must pass sequentially from the NaI(Tl) crystal through the silicone gel interface, glass window, silicone grease interface, and photomultiplier glass before striking the photocathodes within the photomultiplier tubes. The photocathodes serve to convert the light to electrons by the photoelectric effect and the electrons are amplified (multiplied) in the photomultiplier tubes. Amplified signals generated in photomultiplier tubes in the vicinity of the scintillation event are then mathematically combined by known analog or digital means to determine the position and the energy of the gamma-ray absorption in the crystal.

The accurate determination of the energy level and position of the scintillation event requires that the efficiency of transmission of the scintillation light to the photomultiplier tubes be high. Also, since the distribution of the light transferred to an array of photomultiplier tubes from the origin of a scintillation event is used computationally to determine position, light dispersion or deflection which adversely modifies the distribution degrades the position determination. For example, if light is reflected back from an interface and possibly undergoes multiple reflections before striking a photocathode, the position information contained in the photomultiplier signals received is likely to be compromised. Thus, it is important to minimize the probability of back reflections occurring at an interface of optically coupled materials having different indices of refraction by reducing the number of interfaces, matching the indices of refraction as closely as possible, and directing the light by means that will enhance transmission through interfaces to the receiving photocathodes.

The design of a conventional scintillation camera is subject to several optical constraints dictated by the rigid geometry of planar or curved sandwiches of crystal, glass, and intermediate optical coupling materials. By far, the most difficult light transfer occurs at the surface of the crystal leading to the glass interface. The crystal has an index of refraction of about 1.85 and the glass index is typically about 1.54. Currently silicone gel material having an index of about 1.42 is used to couple the crystal to the glass. The gel has good mechanical interfacing characteristics and transmissivity but its index of refraction is a poor match to the crystal and the glass with regard to light transmission through the interfaces. Other materials with indices closer to that of the glass have been employed but their mechanical coupling characteristics are inferior. Light from the crystal which strikes the gel interface at angles of incidence greater than 50 degrees is totally internally reflected totally back into the crystal. This internal reflection may be repeated many times between the exit and the entrance faces of the crystal, as in a light pipe, unless the surfaces of the crystal and the internal reflections thereon are diffuse enough to alter the direction of the light rays so as to lower some of the angles of incidence on successive reflections. In the process, the quantity of light transmitted is diminished by light absorption and its distribution, diffused by reflections, results ultimately in degraded energy and position resolution.

Another problem of curved surface cameras, such as cameras of annular, arcuate or hemispherical design, is that the unfavorable expansion coefficients of the crystal, silicone gel coupling material and the glass cause each of them to expand and contract in opposition to the others with increasing or decreasing temperatures. As the temperature increases, pressure is put on the glass and crystal possibly causing fracture. As the temperature drops, the silicone gel may de-couple from either the glass or the crystal and light may be prevented from passing from the crystal to the glass. Consequently, curved surface cameras made by conventional methods may have a limited operating temperature range between approximately 60° F. to 80° F., for example. Shipping temperature range is also limited which significantly adds to the cost of transportation.

Yet another problem is that crystals for scintillation cameras must generally be constructed from a single optically continuous crystal material. Otherwise an optical discontinuity will result in back reflections at the discontinuity interfaces which disrupt the direction of light transmission to the photomultipliers generally making it impossible to image by usual scintillation camera methods. In some instances, such as the construction of a curved surface camera, for example, it is particularly costly to construct an annular crystal system using an optically continuous single crystal annulus.

Yet another problem associated with prior art cameras is that their field of view is not optimized. Since all the photosensors are located equidistant from the scintillation material, the geometry of the light collection and the solid angles that the photosensors present to the light scintillations are constrained because only the end windows are directly exposed to light entering the glass from the scintillation material.

Still another problem with prior art cameras is the increased tendency for light emitted by the scintillation material to be reflected back within the scintillation material when the angle of incidence approaches the critical angle for total internal reflection thus lowering the efficiency of the camera. Attempts have been made at roughening the light transmitting surface of the scintillation material by sanding operations (See U.S. Pat. No. 4,631,409), but the reduction of internal reflections and hence any increase in efficiency is non-predictable due to the unknown and often non-repeatable surface geometry characteristics of the scintillation material formed by sanding operations. Still another problem associated with prior art cameras is that it is difficult and often expensive to obtain a single piece of scintillation material which spans the entire field of view of the camera. And, when segments of the scintillation material are mated to each other, the interface causes the light generated by the scintillation material to reflect at the junction thereby affecting the ability to accurately determine the position of the source which generated the light.

SUMMARY OF INVENTION

It is therefore an object of this invention to provide an improved scintillation camera.

It is a further object of this invention to provide such a scintillation camera that has improved light transfer characteristics.

It is a further object of this invention to provide such a scintillation camera with improved efficiency and distribution of light collection.

It is a further object of this invention to provide such a scintillation camera which has improved position and energy resolution.

It is a further object of this invention to provide an improved scintillation camera which eliminates two reflection and refraction boundaries associated with conventional scintillation cameras.

It is a further object of this invention to provide an improved scintillation camera which transmits light rays generated within the scintillation crystal at angles of incidence greater than conventional scintillation cameras before they are totally internally reflected.

It is a further object of this invention to provide an improved annular scintillation camera which is much less temperature sensitive and therefore more robust and operable over a greater temperature range than conventional annular scintillation cameras.

It is a further object of this invention to provide an improved annular scintillation camera having a multi-segmented scintillation crystal.

It is a further object of this invention to provide an improved scintillation camera whose photomultiplier response functions are adjustable by means of reflecting optical baffles to direct the light transmissions.

It is a further object of this invention to provide such an improved scintillation camera in which has a field of view that extends closer to the edge of the camera.

It is a further object of this invention to provide such an improved scintillation camera which can tomographically image close to a body, such as the chest wall during examination for tumors in a pendant breast.

It is a further object of this invention to provide such an improved scintillation camera, which because of its improved field of view, resolution and sensitivity, enables earlier detection of tumors of smaller size.

It is a further object of this invention to provide such an improved scintillation camera having a liquid optical coupling which is not subject to separation either on formation or over time.

It is a further object to provide such a scintillation camera which has a greater field of view.

It is a further object of this invention to provide such a scintillation camera with an increased efficiency due to a reduction in the internal reflections of light generated by the scintillation material.

It is a further object of this invention to provide such a scintillation camera with improved transmissivity through the scintillation material at the interface between two scintillation material segments.

This invention results from the realization that the field of view of a scintillation camera can be increased by raising the height of the end windows of the photodetectors located at the edge of the scintillation material and by forming side windows in all adjacent lower level photodetectors to thereby permit position determination of sources of radiation even closer to the edges of the camera.

This invention results from the further realization that a truly more accurate and versatile scintillation camera having greater energy and spacial resolution can be achieved by replacing the glass window and all the intermediate interfaces of the conventional scintillation cameras with a liquid interface medium and that using the liquid interface medium instead of a planar glass window allows certain photodetectors to be raised and arranged at different heights as desired to increase the field of view of the camera.

This invention results from the further realization that internal reflections of light generated by the scintillation material can be reduced in a predictable fashion by increasing the surface area of the light transmitting surface of the scintillation material via a predetermined pattern of peaks and valleys to increase the efficiency of the camera.

This invention results from the further realization that the transmissivity throughout a scintillation material formed in discrete segments can be improved by increasing the surface area at the interface between two such segments and forming a series of angled grooves in one segment which mate with peaks formed in the other segment at the interface thereby improving the optical coupling of the adjacent segments at the interface between them.

This invention features a scintillation camera comprising photosensor means for producing an output in response to emitted light and a scintillation material for emitting light directed to the photosensors means in response to radiation absorbed by a source wherein the scintillation material is formed in two or more segments defining an optical interface between adjacent segments. There are means for increasing the surface area at the interface for improving the transmissivity of the interface and efficiently optically coupling the adjacent segments.

The means for increasing the surface area may include a plurality of peaks and valleys formed in each segment at the interface, the peaks of one segment mating with valleys of the other segment at the interface. The valleys are preferably angled grooves formed in the scintillation material. The groove angle is usually less than or equal to the critical angle of incidence for total internal reflection in the scintillation material.

The peaks and valleys may extend between a top and bottom surface of the scintillation material or instead extend longitudinally across the interface between the two scintillation material segments. The interface may be orthogonal with respect to the plane of the scintillation material or angled with respect to the plane of the scintillation material.

There may also be a liquid interface medium for optically coupling the segments of scintillation material. The scintillation material is typically a scintillation planar, arcuate, or annular crystal. The liquid interface medium preferably has an index of refraction between the indices of refraction of the photosensor means and the scintillation material such as between approximately 1.52 and 1.67. The liquid interface medium directly couples the emitted-light from the scintillation material to the photosensor means.

DISCLOSURE OF PREFERRED EMBODIMENT

Other objects, features and advantages will occur to those skilled in the art from the following description of a preferred embodiment and the accompanying drawings, in which:

FIG. 5 is a cross-sectional view of another scintillation camera in accordance with the subject invention;

FIG. 6 is a schematic view of a single set of parallel grooves formed in the light transmitting surface of the scintillation camera shown in FIG. 5;

FIG. 7 is a schematic view showing two sets of parallel, orthogonally oriented grooves formed in the light transmitting surface of the scintillation material of the camera shown in FIG. 5;

FIG. 8 is a schematic view showing sets of grooves that form a honeycomb pattern in the light transmitting surface of the scintillation material of the camera shown in FIG. 5;

FIG. 11 is a cross-sectional view of another yet embodiment of a two dimensional scintillation camera in accordance with the subject invention including retro-reflectors formed in the gamma ray entrance surface of the scintillation material;

FIG. 12 is a schematic view of one embodiment of the retro-reflectors shown in FIG. 11 formed as a set of parallel grooves;

FIG. 13 is a schematic view of another embodiment of the retro-reflectors shown in FIG. 11 formed as two sets of orthagonal grooves;

FIG. 14 is a schematic view of another embodiment of the retro-reflectors shown in FIG. 11 formed as a honeycomb pattern;

Figure 1:
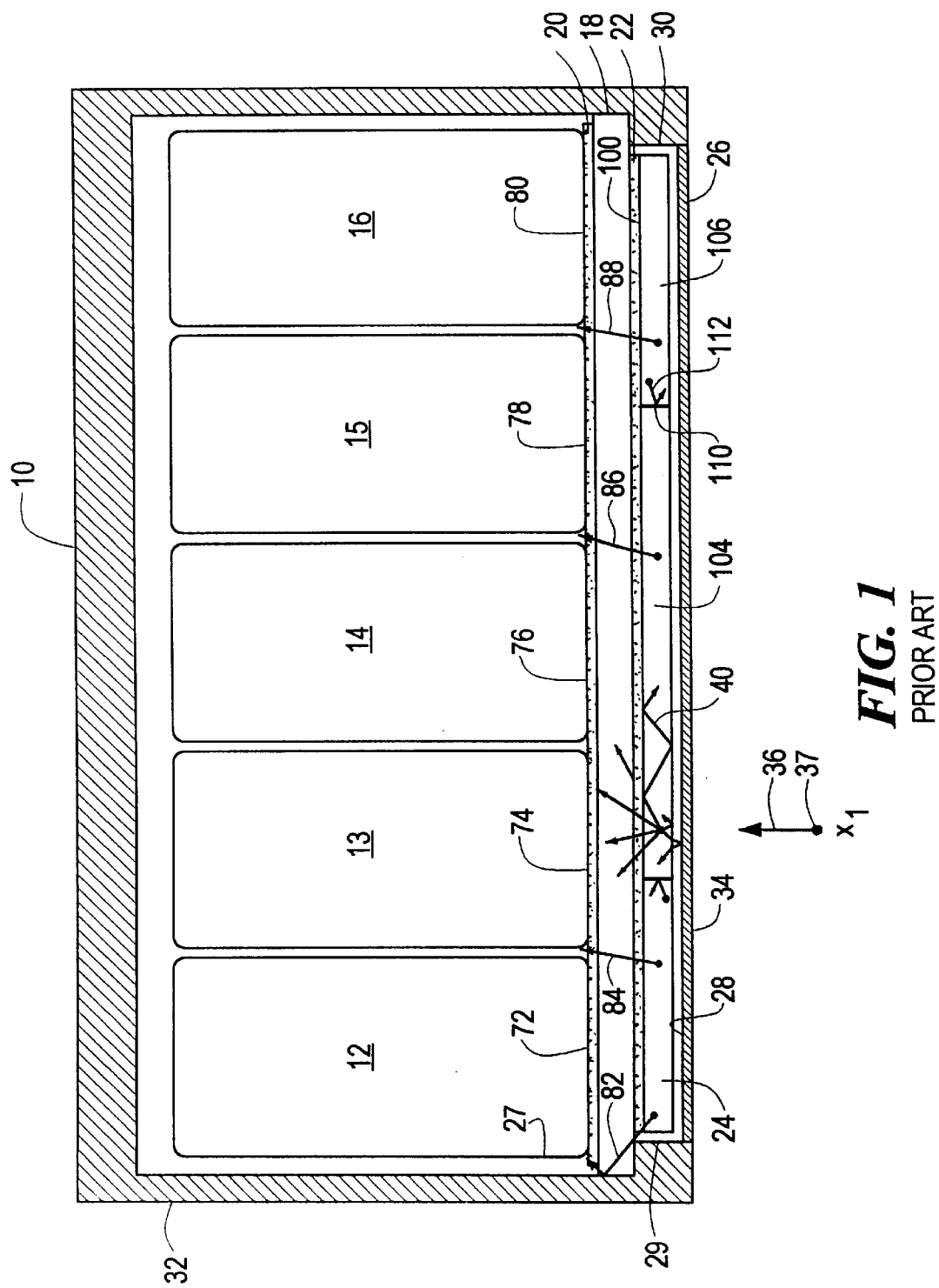
FIG. 1 is a cross-sectional view of a two dimensional prior art scintillation camera.

There is shown in FIG. 1 a cross-sectional view of a conventional planar scintillation camera 10 having a rectangular array of photosensors, namely photomultiplier tubes 12–16 positioned above glass window 18. There is included a film of silicone grease 20 which acts as an optical coupling agent between the photomultiplier tubes and one surface of glass window 18. On the opposite surface of glass window 18 is a layer of clear silicone gel material 22 which acts as an optical coupling agent or interface between glass window 18 and radiation detection means, namely scintillation crystal 24. The crystal is typically a thallium activated sodium iodide (NaI(Tl)) crystal. Crystal 24 is enclosed in a hermetically sealed container 26 filled with dry gas located within area 28. The ends 29 and 30 of container 26 may be coated with either a light absorbing material or they may be made reflective. These components are contained within camera housing 32 which includes an opaque gamma-ray entrance window 34 that allows gamma radiation indicated at arrow 36 emanating from source 37 at $X_i$ to pass therethrough and be received by scintillation crystal 24. Entrance window 34 is typically aluminum and made highly internally reflective, but it may be formed of any material which is similarly transparent to gamma radiation.

Gamma-rays emitted from source 37 are converted to scintillation light emissions 38 at the point of absorption by scintillation crystal 24, some of which pass through glass window 18 and are received by two or more photomultipliers 12–16. The photomultipliers convert the light received into electrical signals. Those signals exceeding a prescribed threshold are then combined mathematically by known techniques to determine the locations of gamma-ray absorption in the crystal from their scintillation events. Image formation from a large number of scintillation events is then accomplished by known techniques. This conventional camera configuration thus includes four refraction and reflection boundaries between the crystal and the photomultipliers, namely, the boundaries between the crystal 24 and silicone gel 22, gel 22 and glass window 18, glass window 18 and the silicone grease 20, and grease 20 and photomultipliers 12–16. Typically, the indices of refraction of the photomultiplier tubes 12–16, optical coupling grease 20 and glass 18 are reasonably well matched in the range of 1.46 to 1.53. However, the crystal 24 with an index of refraction of 1.84 as compared to silicon gel 22 with an index of refraction of about 1.42 and the glass 18 with an index of refraction of about 1.53 are poor matches. Light incident from the scintillation event 38 on the crystal 24 to gel 22 interface at angles of incidence, φ, greater than 50° are totally internally reflected as indicated by reflected ray 40 and will likely be reflected along the path of the crystal unless deflected favorably to lower angles of incidence by diffuse surfaces at the entrance face or gel boundary after one or more encounters. Internal reflection disperses the light signal from scintillation event 38 generally degrading the distribution of light reaching photomultipliers 12–16 and the resulting position determination and image resolution.

The amount of light received from scintillation event 38 by each of the photomultipliers 12–16 through gel 22, glass 18 and coupling grease 20 is governed by the interface transmission characteristics, the locations of the photomultipliers relative to the scintillation event, and the dimensions of crystal 24, glass window 18, and gel interface 22. The solid angle of light received directly by photomultipliers 12–16 from scintillation emission event 38 are important parameters in camera design which, together with more dispersed back reflections from the bottom surface of the crystal 24 which is not coupled to gel 22, largely define photomultiplier response functions. In conventional designs these angles are fixed by geometries of the glass, gel and crystal and cannot be altered without changing the structure and hence, the quality of the response functions cannot be modified without re-fabricating the camera.

The response of such a prior art camera is delineated in U.S. patent application Ser. No. 08/543,870 filed Oct. 19, 1995 entitled "Liquid Interface Scintillation Camera," now allowed, which is incorporated herein by this reference. Also, the improvements and advantages of eliminating glass window 18 and replacing it with liquid interface medium 60, FIG. 2 with an index of refraction of between approximately 1.40 and 1.67 are fully described in the aforesaid patent application and not repeated herein.

As delineated in the Background of the Invention above, another problem with prior art camera 10, FIG. 1, is the limited field of view. Since photosensors 12–16 all have end windows 72–80, respectively, located equidistant from scintillation material 24, the geometry of light collected and the solid angles that the photosensors present to the light scintillation are constrained because only the end windows are directly exposed to light entering the glass from the scintillation material. For example, light rays 82, 84, 86, and 88 will not be detected by any photosensors.

The other problem with camera 10 as delineated in the Background of the Invention above, is that rays, such as ray 40 whose angle of incidence on light transmitting surface 100 facing photosensors 12–16 is greater than the critical angle, are reflected totally back within scintillation material 24 thus decreasing the efficiency of camera 10.

Still another problem with camera 10 as delineated in the Background of the Invention above, is that the transmissivity of scintillation material segments 104 and 106 at smooth interface 110 is poor as shown for light ray 112. Interface 110 causes the light generated by the scintillation material to reflect as shown thus undesirably affecting the ability to determine the position of the source which generated the light. Such reflections are further exacerbated by the layer of air (index of refraction=1.00) between segments 104 and 106 and which separates the higher index (1.84) segments.

Figure 2:
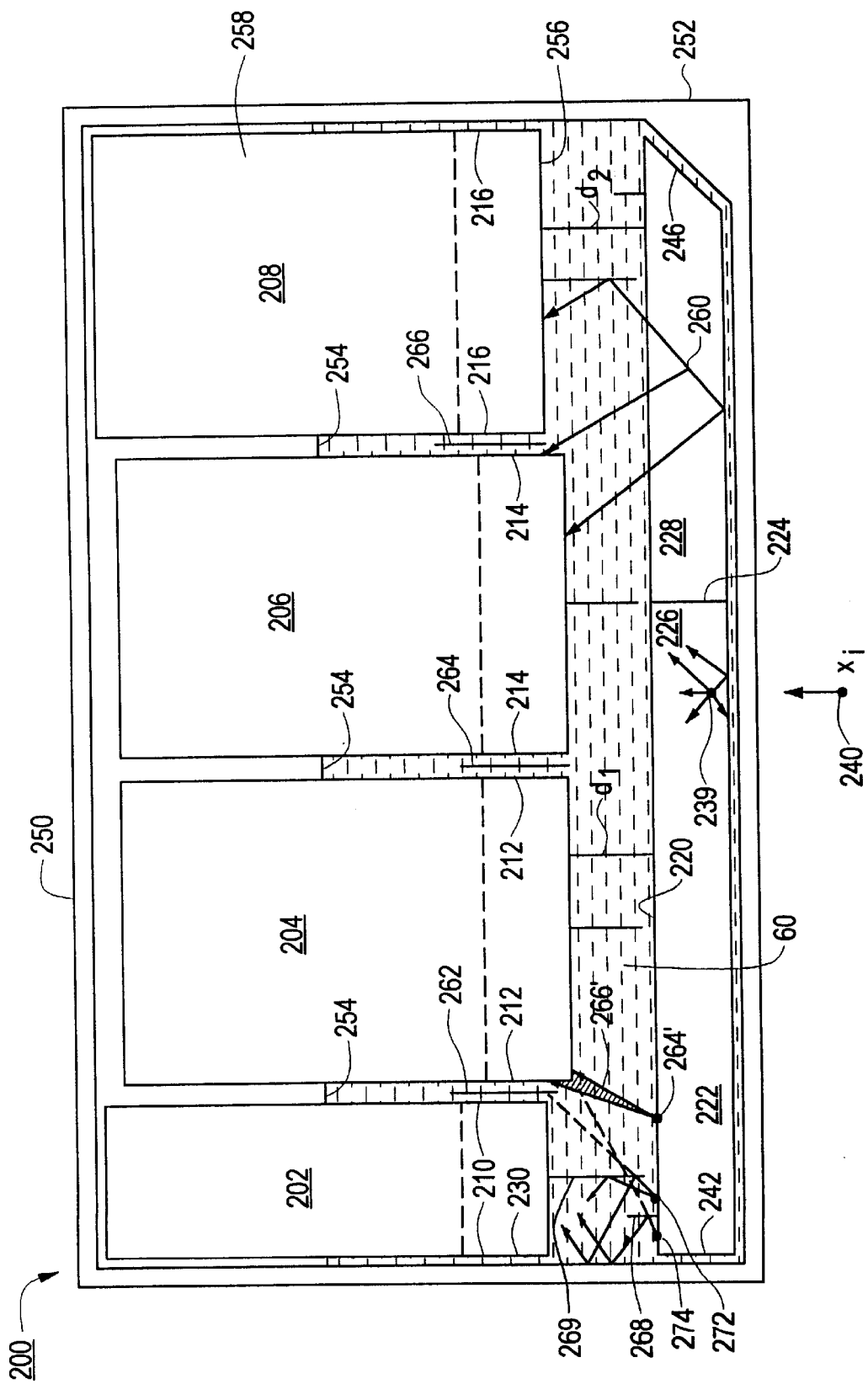
FIG. 2 is a cross-sectional view of the preferred embodiment of the two dimensional scintillation camera of this invention.

All of these problems are overcome in scintillation camera 200, FIG. 2, which may include liquid interface medium 60; raised edge photosensors 202 and 208; side windows 210–216 on each photosensor 202–208, respectively; a predetermined pattern of peaks and valleys formed in light emission surface 220 of scintillation layer 222 (discussed in more detail with reference to FIGS. 5–14); and means for increasing the surface area of interface 224 via a predetermined pattern of peaks and valleys between adjacent scintillation material segments 226 and 228 (discussed in more detail with reference to FIGS. 15–20).

In general, raised edge photosensors 202 and 208 in combination with side windows 212 and 214 increase the field of view of camera 200 and allow imaging to within 4–6 mm of edge 230 of photomultiplier tube 202 in contrast to 25 mm of edge 27, FIG. 1 of tube 12 of prior art camera 12 with equidistant photosensors.

Also, the predetermined pattern of peaks and valleys formed in light transmitting surface 220, FIG. 2, of scintillation layer 222 increases the efficiency of camera 200 for the transmission of light through surface 220 compared to camera 10, FIG. 1, with a planar light transmitting surface 100.

Finally, the means for increasing the surface area of interface 224, FIG. 2, between adjacent scintillation material segments 226 and 228 greatly improves the optical coupling of adjacent segments to provide a highly efficient means for propagating light between two discrete segments.

Each improvement is discussed in turn.
The Raised Edge Photomultipliers

Scintillation camera 200, FIG. 2, includes radiation detection means 222, typically a layer of scintillation material for emitting light as shown at 239 in response to radiation absorbed from source $X_i$, 240. A first plurality of photosensors 204, 206, typically photomultipliers, are disposed at a first distance $d_1$ from the scintillation layer 222 and responsive to it for providing an output in response to emitted light 239.

A second set of photosensors, however, set 202 and 208 located proximate edges 242 and 246 of scintillation material 222 are disposed at a second distance $d_2$, greater than $d_1$ as shown for photosensor 208 for increasing the field of view of the camera. Liquid scintillation camera 200 is thus designed to image closer to the camera's edge. Camera 200 features unconventional placements of the photomultipliers and methods of exposure of their photocathodes to light. Photomultiplier tubes 202–208 are partially emersed in a silicone liquid 60 in container 250 having front and side walls 252 and an upper boundary 254. Photocathodes 256 and 216 are films of photoelectric emitter deposited on the inside surface of the glass bulb which are responsive to the energies received from the light emissions generated in scintillation crystal 222. Also, in the inside surface of the photomultiplier is deposited a ring shaped coating of aluminum 258 to define the potential of the photocathode and the active photocathode surface, namely the photocathode surface that is not covered by aluminum and is exposed to light. As shown in FIG. 2, according to this invention, the 20 photocathodes are exposed at their front (end-window) 256 and in rings along the lower perimeters 216 forming side windows of tubes 202 and 208. See U.S. Pat. No. 5,442,179 incorporated herein by this reference. The depth of the tube emersion 254 goes beyond all of the photocathode surfaces so that the emitted light 260 may reach the side wall photocathode surfaces 216 as well as the end window 256 portions of the photocathodes. Reflecting baffles 262–266 may be used to direct light that may enter the crevices between the tube to the side walls of the photocathode surfaces.

In this embodiment, photomultiplier 202 is smaller than the others to permit imaging closer to the camera's edge. To further tailor the photomultipliers response functions, tube 202 is recessed from the scintillation crystal 222 further than its adjacent tube 204. As a consequence, photomultiplier 204 subtends a larger solid angle for light exiting from the surface point 264' of crystal 222 by the amount indicated by shading 266'. In addition, baffles 268 and 269 serve to direct light increasingly towards tube 202 rather than tube 204 as light 272 and 274 exits closer to the leading end of crystal 222.

At the opposite (right) side of camera 200, a similar displacement of photomultiplier 208 away from the crystal is used to also extend the field of view toward the camera's edge by similar photocathode and reflecting baffle arrangement. In this case, recess tube 208 is the same width dimension as tube 206. Since it may not be necessary or possible to image as close to the edge of the camera in this case, because of larger size of tube 208, the crystal need not reach all the way to the camera's edge and may be alternatively tapered to preferentially reflect light out of crystal 222 towards photomultiplier 208 further enhancing the ability of the camera to image closer to its edge.

Figure 3:
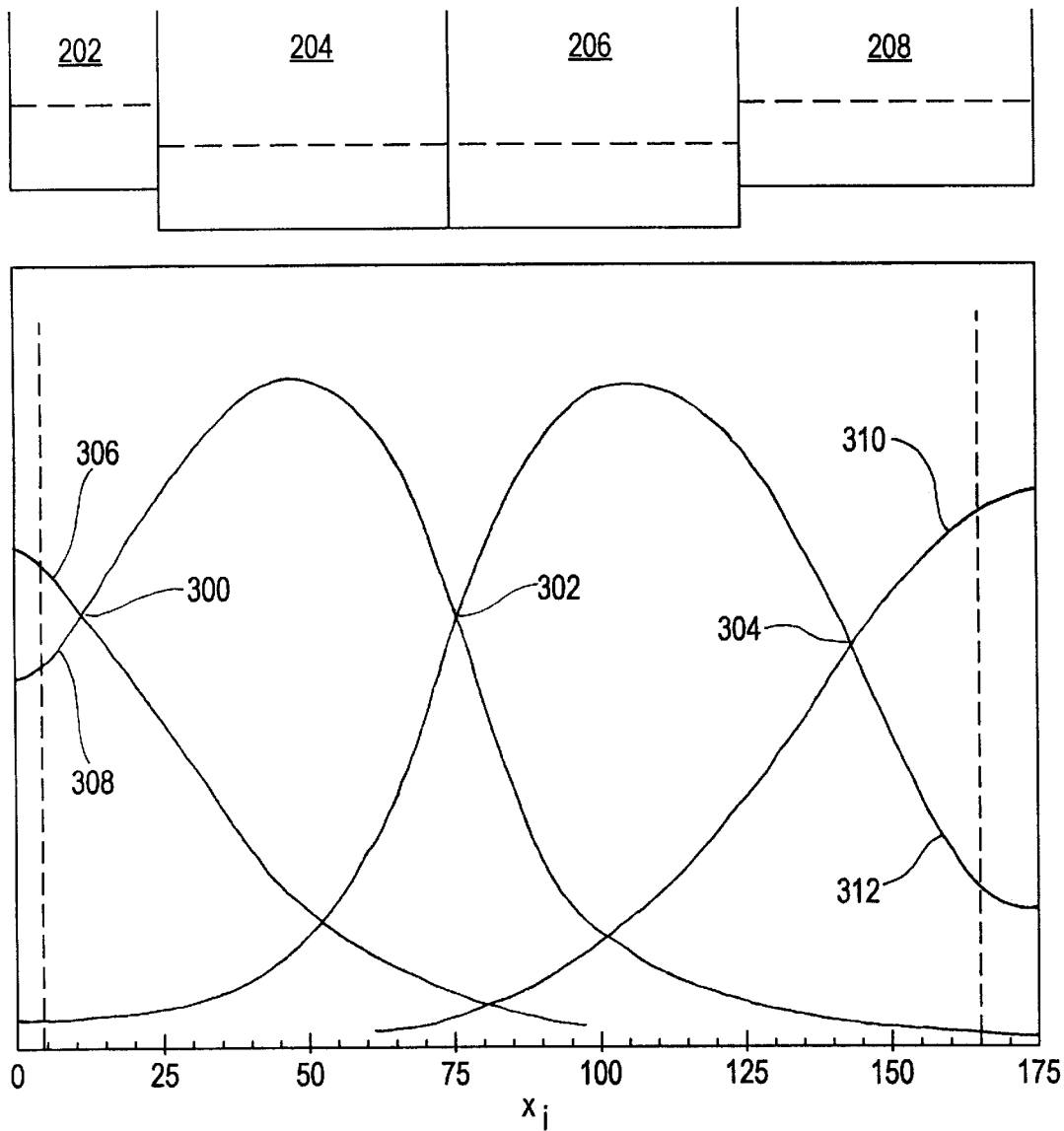
FIG. 3 is a plot of the response of the raised edge photomultipliers of the camera shown in FIG. 2.

FIG. 3 shows the photomultiplier response functions for camera 200 of FIG. 2 in which the amount of light received by a photomultiplier is shown as a function of the position $x_i$ (in millimeters) of emission of light from the scintillation crystal as a result of gamma-ray emissions. Intersections 300, 302 and 304 are the loci of emissions that give rise to equal responses in the adjacent photomultipliers 202 and 204, 204 and 206, and 206 and 208, respectively. Typically, the response functions from adjacent photomultipliers that are positioned at the same distance, such as $d_1$ FIG. 2, from the surface of scintillation material 220 intersect in the proximity of the facing edges of the two photomultipliers generating the responses. Thus, intersection 302 for tubes 204 and 206 is shown to lie almost symmetrically between the two tubes. This response is shown in more detail for conventional camera 10, FIG. 1, in referenced U.S. patent application Ser. No. 08/543,870.

However, the positions of the intersection 300 of the responses of adjacent pair of tubes 202 and 204 and the intersection 304 of adjacent pairs 206 and 208 are displaced outwardly as compared to conventional cameras due to tubes 202 and 208 being raised as discussed above.

This translation of the intersection 300 and 304 towards the ends of the camera and the increasing share of emitted light transferred to tubes 202 and 208 as their respective edges are approached results in slopes 306 and 308 of the functions on the left side of the camera that are large enough to permit position determination by well known position analysis means.

Similarly, slopes 310 and 312 are sufficient to permit good position analysis near the right side of the camera. If, for example, a 1-inch wide tube is used for tube 202 and 2-inch wide tubes are used for the remaining tubes 204–208, the camera will image 4 to 6 millimeters from the edge of photomultiplier 202 and about 10–12 millimeters from the edge of tube 208 with good resolution, whereas, conventional camera 10 using 2-inch equidistant tubes typically image to about 25 millimeters from the edge of an end tube.

Figure 4:
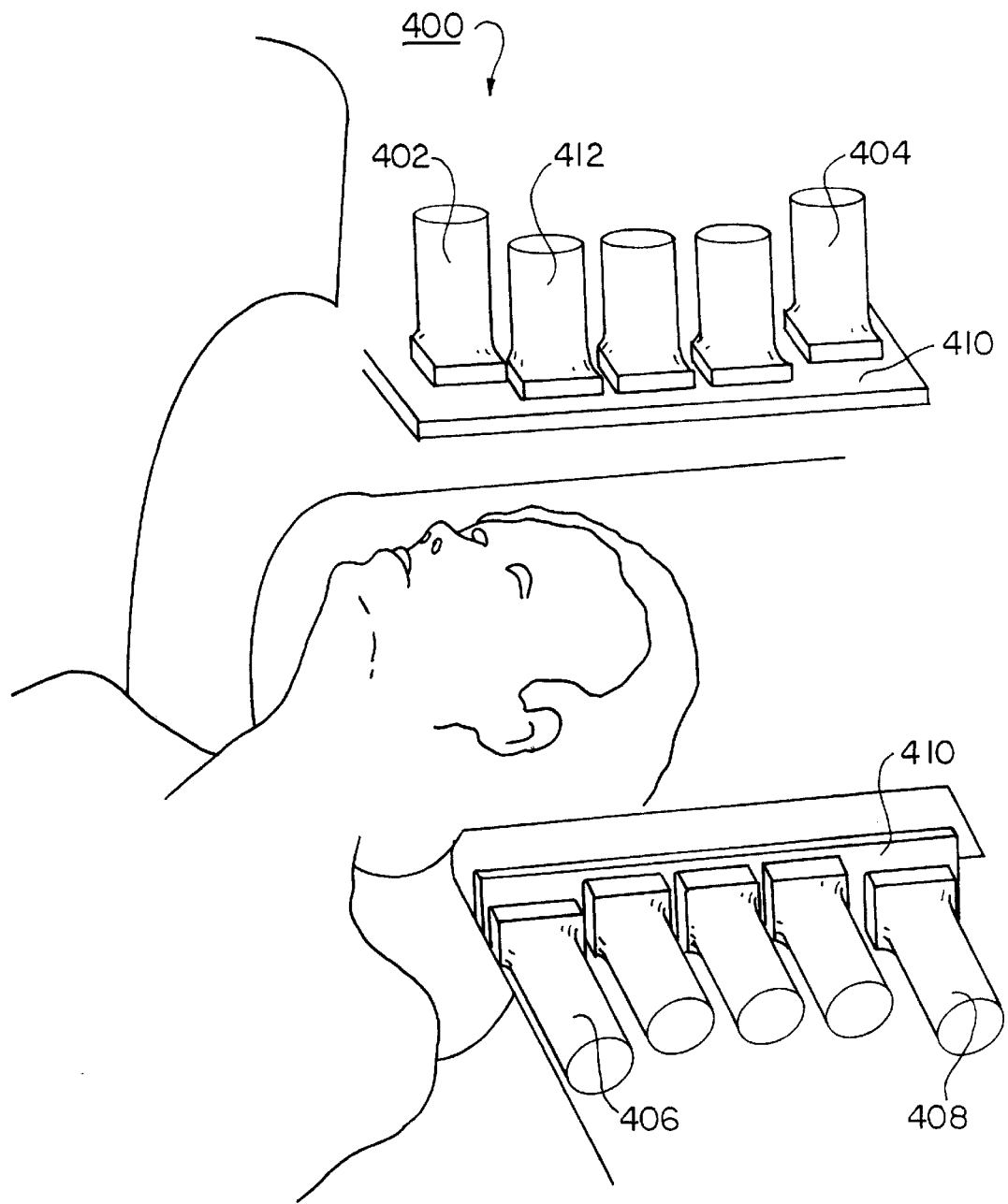
FIG. 4 is a schematic partial three-dimensional view of an annular scintillation camera in accordance with the subject invention.

The axial cross-section of camera 200 shown in FIG. 2 may be representative of the axial cross-section of an annular camera, as shown at 400, FIG. 4, or a cross-section of a planar camera. As shown in FIG. 4, edge photomultipliers 402, 404, 406, and 408 are raised higher above the scintillation layer 410 than the central photomultipliers, e.g. photomultiplier 412. The height $d_2$, FIG. 2 of photomultiplier 208 with respect to distance $d_1$ is typically set such that end window 256 is half way or intermediate the extent of side window 214 of adjacent photomultiplier 206. The same is true for raised photomultiplier 202. Scintillation crystal 222 may be planar, annular, arcuate, polyhedral or hemispherical depending on the specific camera geometry.

The Improved Light Transmitting Surface

Liquid scintillation camera 500, FIG. 5, also includes scintillation layer 502, photosensors 504, 506, 508, and 510 emersed in liquid interface medium 511 all located equidistance from scintillation layer 502. In this embodiment, light transmitting surface 512 of scintillation layer 502 which transmits light to the photosensors includes a predetermined pattern of peaks which may form a series of ridges and valleys as shown in FIGS. 6–7 for reducing the internal reflection of light emitted at point 514, which, if incident on a smooth interface as shown at 516 at an angle greater than the critical angle, would internally totally reflect as shown at 518. Peaks and valley pattern 512, however, decreases the amount of light that is reflected back into scintillation layer 502 from light transmitting surface 512 as shown at 516.

Surface 512 of the crystal facing the photomultipliers is cut into grooves by machining which may be formed alternatively by a set of parallel grooves, FIG. 6, two parallel sets of orthogonally oriented grooves, FIG. 7, or grooves cut into a honeycomb pattern, FIG. 8. Typically, the grooves are cut so as to form truncated triangular cuts, FIG. 6, truncated rectangular prisms, FIG. 7, or truncated hexagonal prisms, FIG. 8. In this application, the truncated grooves are used to enhance transmission from a high index of refraction crystal, such as NaI(TI) having an index of 1.84, into a lower index medium, such as a silicone oil 511 or crystal-to-glass interfacing material 22, FIG. 1 having indices which are typically between 1.42 to 1.6.

Figure 9:
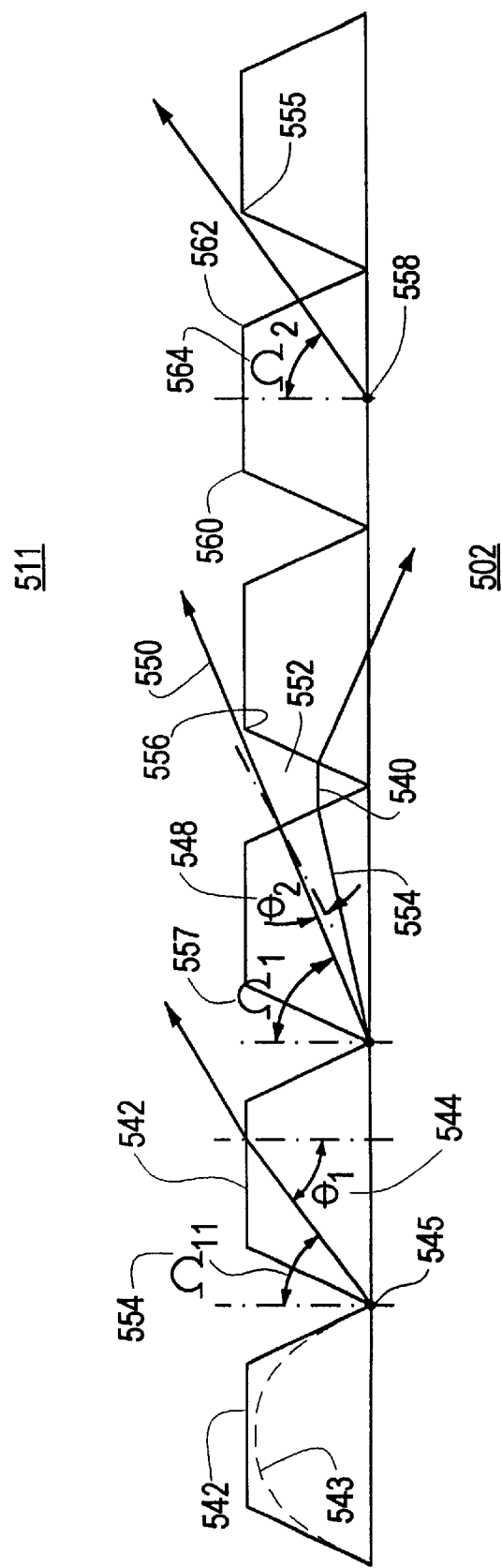
FIG. 9 is an end view of the groove structure shown in FIG. 6.
Figure 10:
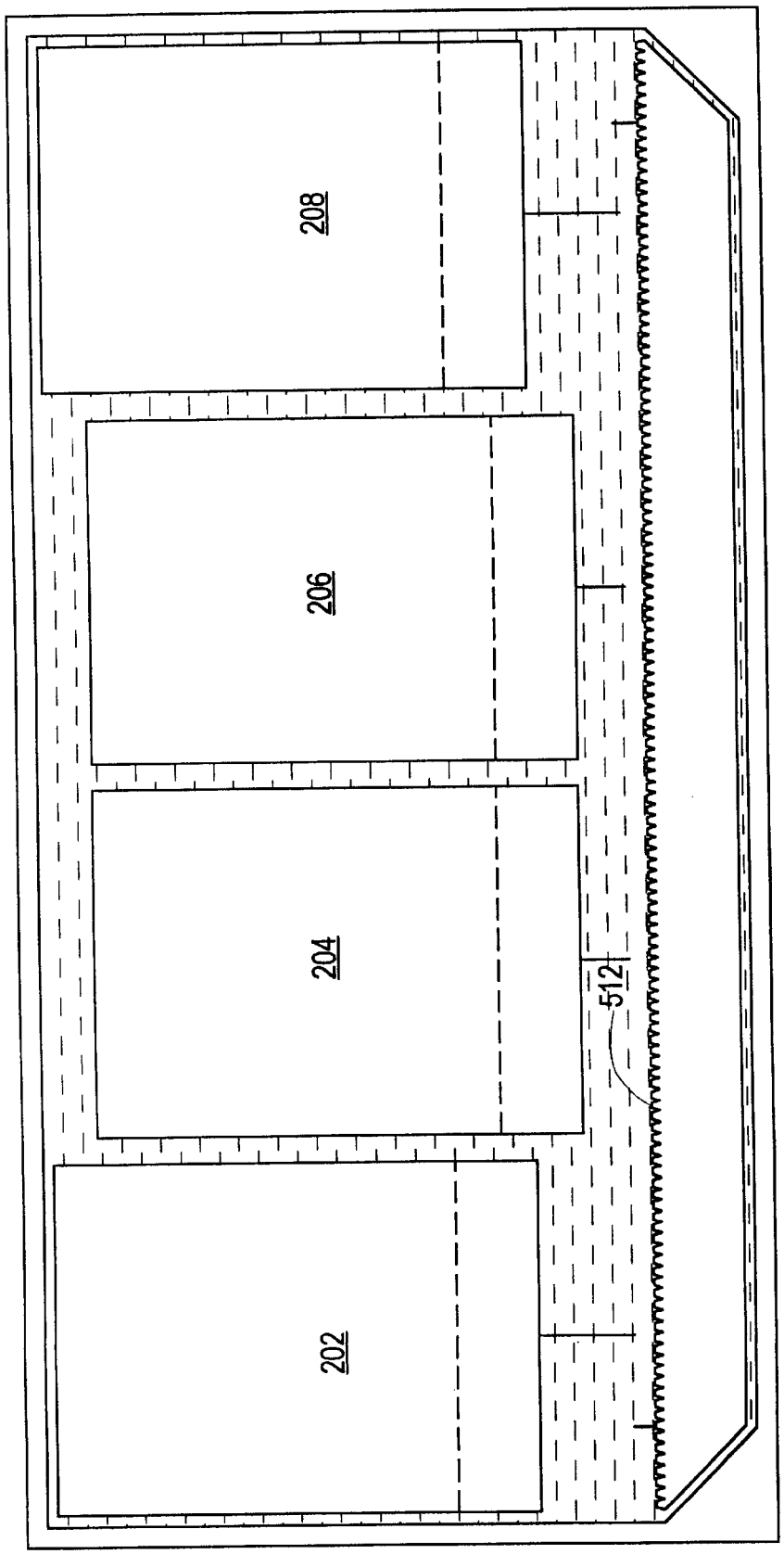
FIG. 10 is a cross-sectional view of yet another embodiment of the two dimensional scintillation camera of the subject invention.

The angle of the cut in the illustration in FIG. 9 is 60° as shown at 540 and the pitch is such as to form semi-hexagonal profiles 542 adjacent to each other. If the index of refraction of crystal 502, FIG. 5 is equal to 1.84 and the index of refraction of interfacing liquid 511 is 1.59, then, in this case, the critical angle for total internal reflection according to Snell's law is 60°. The angle of incidence $\theta_1$, 544, FIG. 9 of the light that strikes the flat truncated surface 542 of the hexagonal profile from a point 545 located near the apex of the triangular grooves is always less than or equal to 60°, so that light will transmit favorably through these co-planar surfaces 542 in accordance with Snell's and Fresnel's laws for reflection and refraction without ever exceeding the critical angle. See John David Jackson, Classical Electro Dynamics, John Wiley and Sons, Inc. The angle of incidence $\theta_2$, 548 for light ray 550 also emitting from the vicinity of an apex and striking the grooved surface is always much smaller than the critical angle for internal reflection and thus light ray 550 transmits into the liquid space 552 efficiently and with minimal internal reflection. When light ray 554 refracts so as to strike below the apex of an adjacent truncated surface 542, ray 554 refracts back into the crystal structure. Thus, ray 550 which passes at the limit of apex 556 defines the maximum angle $\Omega_1$ 557 of the light incident at the crystal liquid interface and can be transmitted therethrough. For the indices and the geometry cited, this angle is about 70° and favorably compares to the critical angle of incidence of 60° for total reflection at a planar surface of the crystal to liquid interface. For a point 558 midway between groove apexes 560 and 562, the maximum angle $\Omega_2$, 564 for light transmission that exits above apex 555 is about 60° which is equal to the critical angle for total internal reflection from a planar surface. However, all rays emitted within the angular extension $\Omega_2$ are incident at their respective interface surfaces at angles less than or equal to 30° and are therefore transmitted with high efficiency in accordance with Fresnel's laws.

Furthermore, computer simulation by ray tracing, using Snell's and Fresnel's laws for reflection and refraction demonstrate that light emitted from a scintillation event in the crystal transmits more efficiently through the interface of the groove structure than through a planar interface surface regardless of the points of origin of the scintillation. In the embodiment shown in FIG. 10, grooved surface 512 is combined with raised edge photomultipliers 202, 208, and the other components of the camera shown in FIG. 2, although this is not a necessary limitation of this aspect of the subject invention. Also, instead of flat surface 542, rounded surfaces as shown in FIG. 9 in phantom at 543 may be formed between adjacent grooves.

Camera 602, FIG. 11, is an alternate embodiment in which the truncated grooves 512 on the upper surface of crystal 604 are combined with retro-reflector gamma ray entrance surface 606. Retro-reflector gamma ray surface 606 is shown alternatively as a set of parallel grooves, FIG. 12, two sets of orthogonal grooves, FIG. 13, or three sets of orthogonal grooves, FIG. 14. These grooves may be coated with highly reflective material as is common practice, or filled with a reflective paste. In combination, these grooves further enhance transmission through the top of the crystal by reflecting light more efficiently and in narrower cones of reflection towards the top surface of the crystal.

The Improved Scintillation Segment Interface

Methods of designing cameras using segmented scintillation crystal segments are delineated in U.S. patent application Ser. No. 08/543,870 filed Oct. 19, 1995 entitled "Liquid Interface Scintillation Camera," now allowed, which is incorporated herein as a reference.

Figure 15:
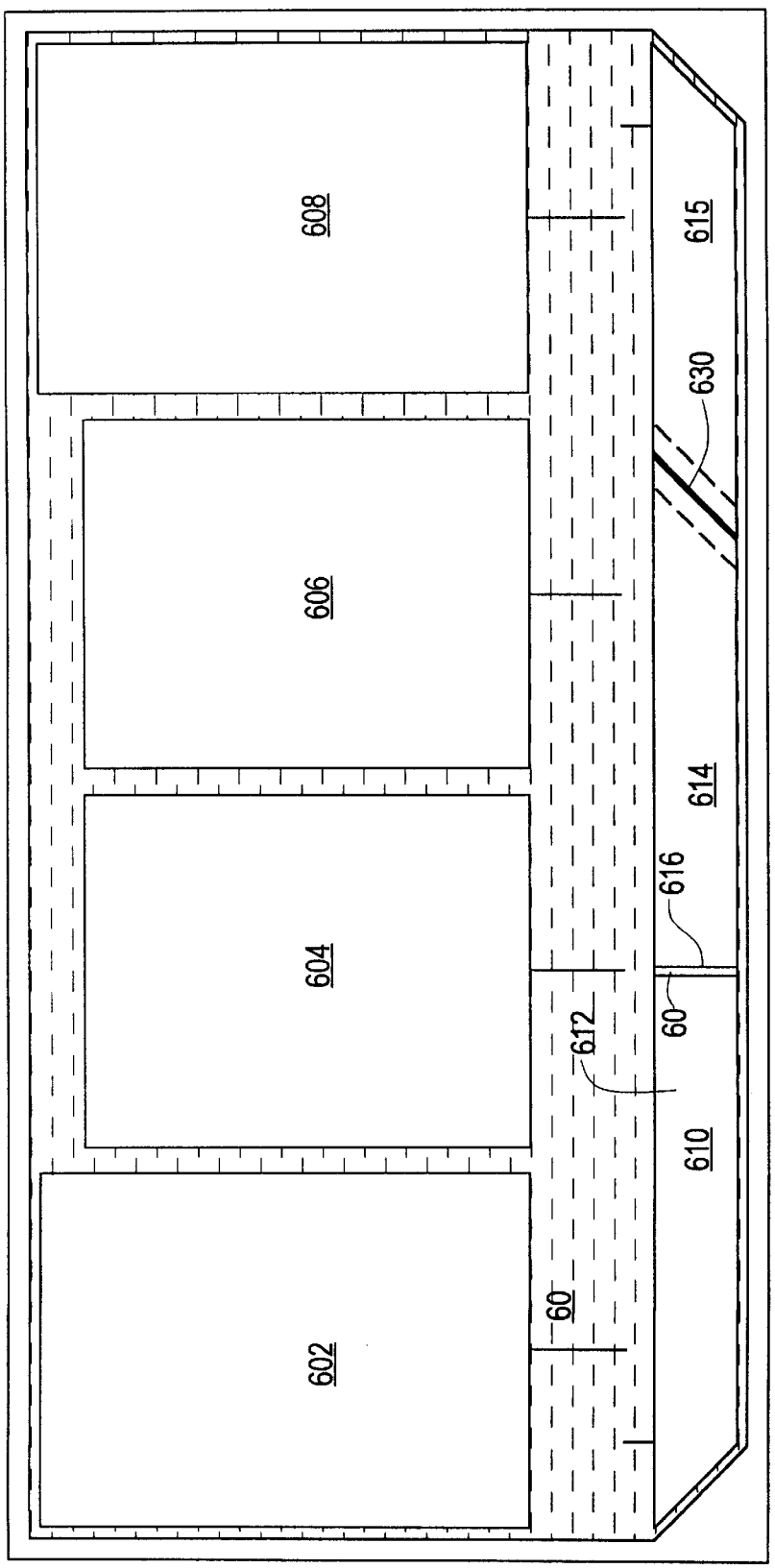
FIG. 15 is a cross-sectional view of another two dimensional scintillation camera in accordance with the subject invention.
Figure 17:
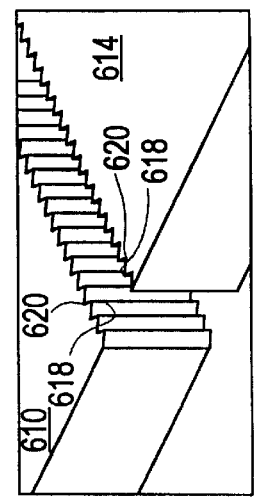
FIG. 17 is a schematic view showing in more detail the increased surface area at the interface between two such scintillation material segments.
Figure 16:
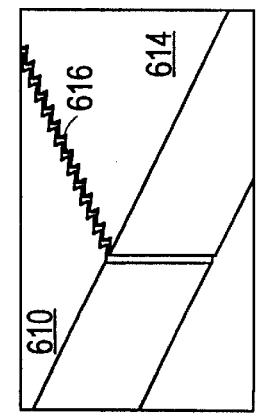
FIG. 16 is a schematic view showing the increased surface area interface between two scintillation material segments in accordance with the subject invention.

Liquid scintillation camera 600, FIG. 15, includes photosensors 602, 604, 606, and 608 equidistance from segmented scintillation material 610 made of segments 612 and 614 defining improved optical interface 616 therebetween, FIG. 16. Interface 616 typically lies approximately along the axis of one photomultiplier such as photomultiplier 604. As shown in FIGS. 16 and 17, the surface area at the interface is increased via peaks and valleys 618, 620, formed in each segment at the interface such that the ridges of one segment mate with the valleys of the other segment at the interface to efficiently optically couple the adjacent segments.

The peaks and valleys are shown in FIG. 16, as matching parallel grooves which are closely fit into each other as required in this embodiment. FIG. 17 is an exploded view of the two segments, 610 and 614, illustrating the groove structure. Since the crystals are preferably immersed in liquid interface medium, a layer of liquid 60 fills the space between the grooves.

Figure 18:
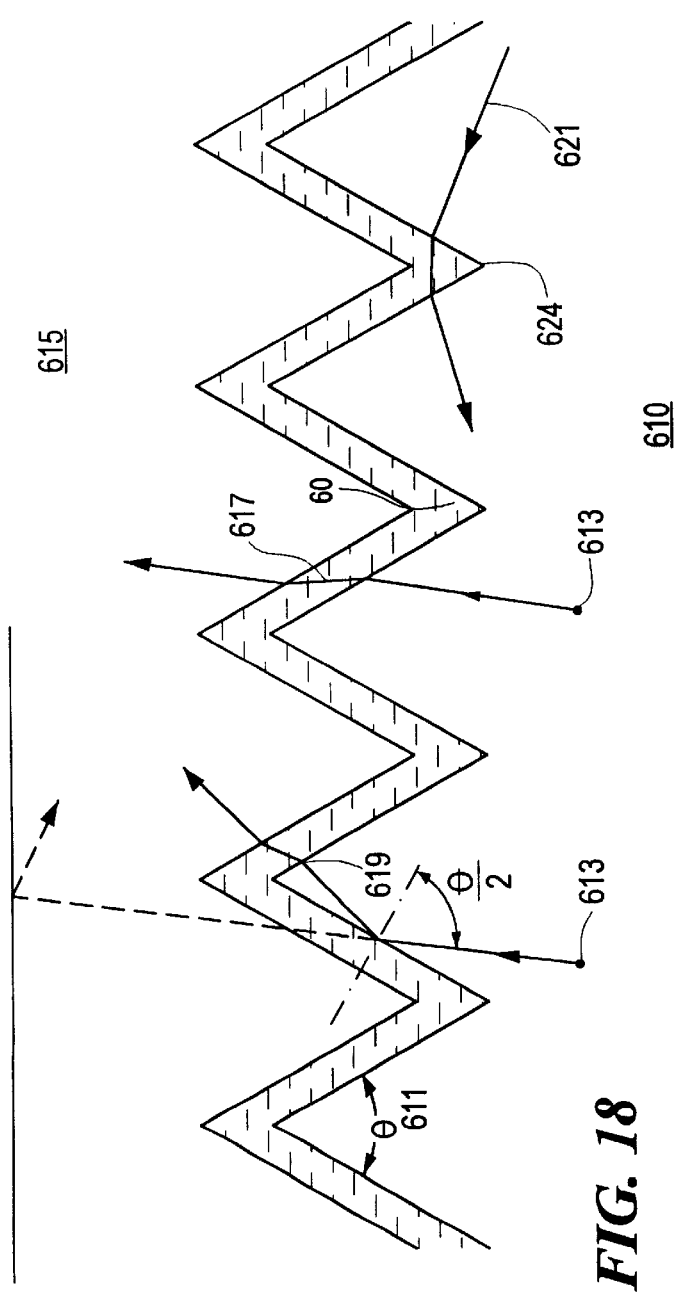
FIG. 18 is a top view of the scintillation material segment interface shown in FIGS. 15–17.

FIG. 18 is a top view of the segment structure and typical light rays traveling in a plane perpendicular to the direction of the ridges and valleys of the grooves. For typical segment and liquid indices of refraction, all but a few percent of the light incident on the junction will either transmit on the first encounter as at 617 or will reflect, either fully or partially, as a light emission point 613 and strike the interface on a second encounter, such as at point 619, at an angle of incidence which is less than or equal to θ/2. Thus, for example, for a crystal index of 1.84, a liquid 60 index of 1.59 and a groove angle ⊖, 611 of 60°, the angle of incidence will be less than or equal to 30°, which is approximately one half the critical angle for total internal reflection and thus results in highly efficient transmission through the groove structure. Thus, light transmits with very high efficiency into the liquid interfacing medium in accordance with Fresnel's law.

Figure 19:
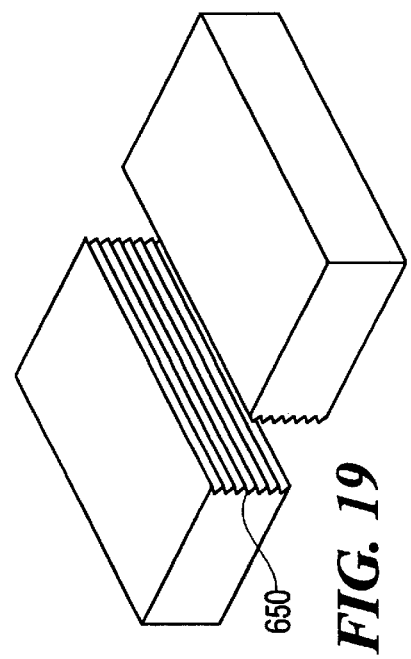
FIG. 19 is a schematic view of another scintillation material segment showing an alternative method of increasing the surface area at the interface between two segments wherein the peaks and valleys extend longitudinally across the interface.

In order to achieve the highest efficiency for light transmission through the interface, it is important to note that the grooves must be close to one another and that the interface between them be thin. For example, light ray 621 striking from the crystal towards liquid 60, in the vicinity of an apex 624 of the crystal may not enter the adjacent crystal and refract back into the crystal when the separation of the grooves is too wide. FIG. 19 shows grooves 650 which are cut longitudinally across the crystal. These grooves perform a similar function as the vertical grooves and may be sets of parallel grooves.

Figure 20:
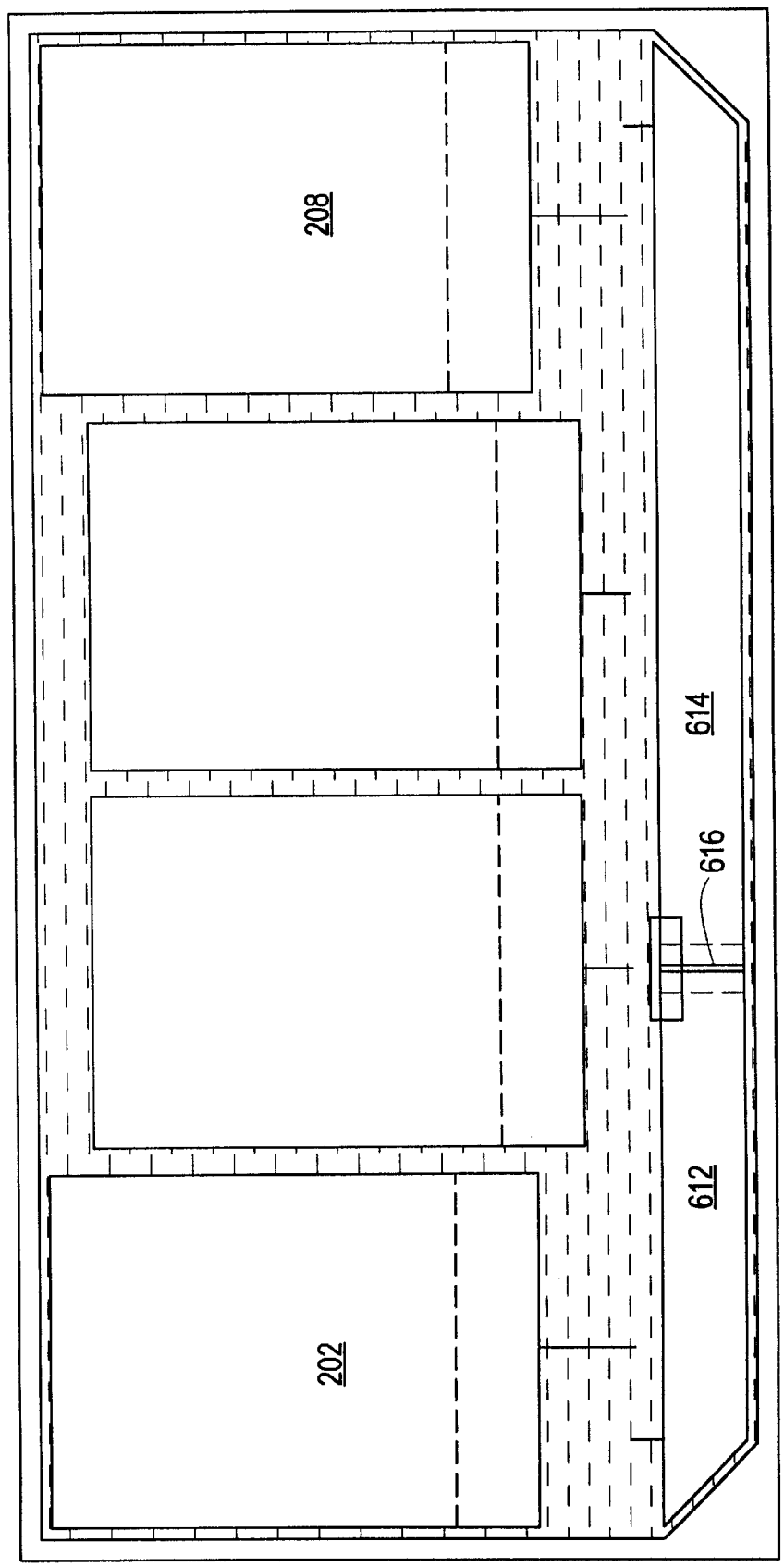
FIG. 20 is a cross-sectional view of another two dimensional scintillation camera in accordance with the subject invention.

In the embodiment shown in FIG. 20, the increased surface area at interface 616 between segment 612 and 614 is shown combined with raised edge photosensors 202 and 208 and this embodiment may be combined with the improved light emissive surface embodiment shown in FIGS. 5–14. Note also that this improved interface surface area embodiment may be easily accomplished in angled interface 630, FIG. 15, between adjacent scintillation segments 614 and 615.

Although specific features of this invention are shown in some drawings and not others, this is for convenience only as each feature may be combined with any or all of the other features in accordance with the invention. For example, the raised edged photomultipliers, the improved light emissive surface, and the improved scintillation segment interface could be used in connection with non-liquid interface prior art scintillation camera 10, FIG. 1, and each such feature could be combined with each other in any of a variety of ways. In the preferred embodiment, liquid interface scintillation camera 200, FIG. 2, includes all three improvements: the raised edge photomultipliers, the improved light emissive scintillation material surface, and if the scintillation material is segmented, the improved scintillation segment interface of this invention.

Other embodiments will occur to those skilled in the art and are within the following claims:

What is claimed is:

1. A scintillation camera comprising:
   photosensor means for producing an output in response to emitted light;
   a scintillation material for emitting light directed to said photosensors means in response to radiation absorbed by a source, the scintillation material formed in two or more segments defining an optical interface between adjacent segments; and
   means for increasing the surface area at the interface for improving the transmissivity of the interface and efficiently optically coupling the adjacent segments.

2. The scintillation camera of claim 1 in which said means for increasing the surface area includes a plurality of peaks and valleys formed in each said segment at the interface, the peaks of one segment mating with valleys of the other segment at the interface.

3. The scintillation camera of claim 2 in which the valleys are angled grooves formed in the scintillation material.

4. The scintillation camera of claim 3 in which the groove angle is less than or equal to the critical angle of incidence for total internal reflection in the scintillation material.

5. The scintillation camera of claim 2 in which the peaks and valleys extend between a top and bottom surface of the scintillation material.

6. The scintillation camera of claim 2 in which the peaks and valleys extend longitudinally across the interface between the two scintillation material segments.

7. The scintillation camera of claim 1 in which the interface is orthogonal with respect to the plane of the scintillation material.

8. The scintillation camera of claim 1 in which the interface is angled with respect to the plane of the scintillation material.

9. The scintillation camera of claim 1 further including a liquid interface medium for optically coupling the segments of scintillation material.

10. The scintillation camera of claim 9 in which said liquid interface medium has an index of refraction between the indices of refraction of said photosensor means and said scintillation material.

11. The scintillation camera of claim 10 in which said liquid interface medium has an index of refraction between approximately 1.52 and 1.67.

12. The scintillation camera of claim 9 in which said liquid interface medium directly couples the emitted light from said scintillation material to said photosensor means.

13. The scintillation camera of claim 1 in which the scintillation material is a scintillation crystal.

14. The scintillation camera of claim 13 in which said scintillation crystals are planar.

15. The scintillation camera of claim 13 in which said scintillation crystals are annular.

16. The scintillation camera of claim 13 in which said scintillation crystal is arcuate.

* * * * *